United States Patent [19]
Aranyi et al.

[11] Patent Number: 5,603,723
[45] Date of Patent: Feb. 18, 1997

[54] SURGICAL INSTRUMENT CONFIGURED TO BE DISASSEMBLED FOR CLEANING

[75] Inventors: Ernie Aranyi, Easton; Douglas J. Cuny, Bethel, both of Conn.

[73] Assignee: United States Surgical Corporation, Norwalk, Conn.

[21] Appl. No.: 371,251

[22] Filed: Jan. 11, 1995

[51] Int. Cl.$^6$ .................................................. A61B 17/00
[52] U.S. Cl. ........................... 606/205; 606/52; 606/174; 128/751
[58] Field of Search ............................... 606/51, 52, 174, 606/205–211; 128/750–755; 604/22

[56] References Cited

U.S. PATENT DOCUMENTS

| | | |
|---|---|---|
| 1,274,669 | 8/1918 | Bohn . |
| 2,113,246 | 4/1938 | Wappler . |
| 2,114,695 | 4/1938 | Anderson . |
| 2,790,437 | 4/1957 | Moore . |
| 4,054,143 | 10/1977 | Bauer . |
| 4,084,594 | 4/1978 | Mosior . |
| 4,122,856 | 10/1978 | Mosior et al. . |
| 4,258,716 | 3/1981 | Sutherland . |
| 4,483,562 | 11/1984 | Schoolman . |
| 4,569,131 | 2/1986 | Falk et al. . |
| 4,674,501 | 6/1987 | Greenberg . |
| 4,819,633 | 4/1989 | Bauer et al. . |
| 4,896,678 | 1/1990 | Ogawa . |
| 4,950,273 | 8/1990 | Briggs . |
| 4,994,024 | 2/1991 | Falk . |
| 5,009,661 | 4/1991 | Michelson . |
| 5,013,300 | 5/1991 | Williams . |
| 5,053,043 | 10/1991 | Gottesman et al. . |
| 5,147,357 | 9/1992 | Rose et al. . |
| 5,147,378 | 9/1992 | Markham . |
| 5,151,101 | 9/1992 | Grossi et al. . |
| 5,172,700 | 12/1992 | Bencini et al. . |
| 5,211,655 | 5/1993 | Hasson . |
| 5,282,800 | 2/1994 | Foshee et al. . |
| 5,282,806 | 2/1994 | Haber et al. . |
| 5,290,308 | 3/1994 | Knight et al. . |
| 5,304,203 | 4/1994 | El-Mallawany et al. . |
| 5,308,358 | 5/1994 | Bond et al. . |
| 5,336,238 | 8/1994 | Holmes et al. .......................... 606/208 |
| 5,368,606 | 11/1994 | Marlow et al. . |

OTHER PUBLICATIONS

ISI Laparoscopic Instruments, Innovative Surgical, Inc., Apr. 1994.
Nu-Tip™, Marlow Surgical Technologies, Inc., 1992.
Take-Apart® Instruments, Karl Storz Endoscopy (undated).
New Arthroscopy Instruments, Eder Instrument Co., Inc. (undated).
Sinus Endoscopy, Smith & Nephew Richards (undated).

*Primary Examiner*—Michael Powell Buiz
*Assistant Examiner*—William Lewis

[57] ABSTRACT

A surgical apparatus is disclosed which includes a handle assembly having a barrel portion, a stationary handle depending from the barrel portion, and an actuating handle pivotally associated with the barrel portion. An elongate body assembly having opposed proximal and distal end portions and an interior bore extending therethrough is releasably engaged within the barrel portion of the handle assembly. An actuation assembly is provided and includes an elongate control shaft dimensioned to extend through the interior bore of the body assembly. A jaw housing is attached to a distal end portion of the control shaft, and a pair of jaw members are supported in the housing. The jaw housing is releasably engaged to the body assembly within the interior bore thereof, and a proximal end of the control shaft is releasably engaged to the actuation handle. A release button is mounted in the barrel portion of the handle assembly and includes a spring biased clasp for releasably engaging the control shaft adjacent the proximal end thereof.

22 Claims, 9 Drawing Sheets

FIG. 5

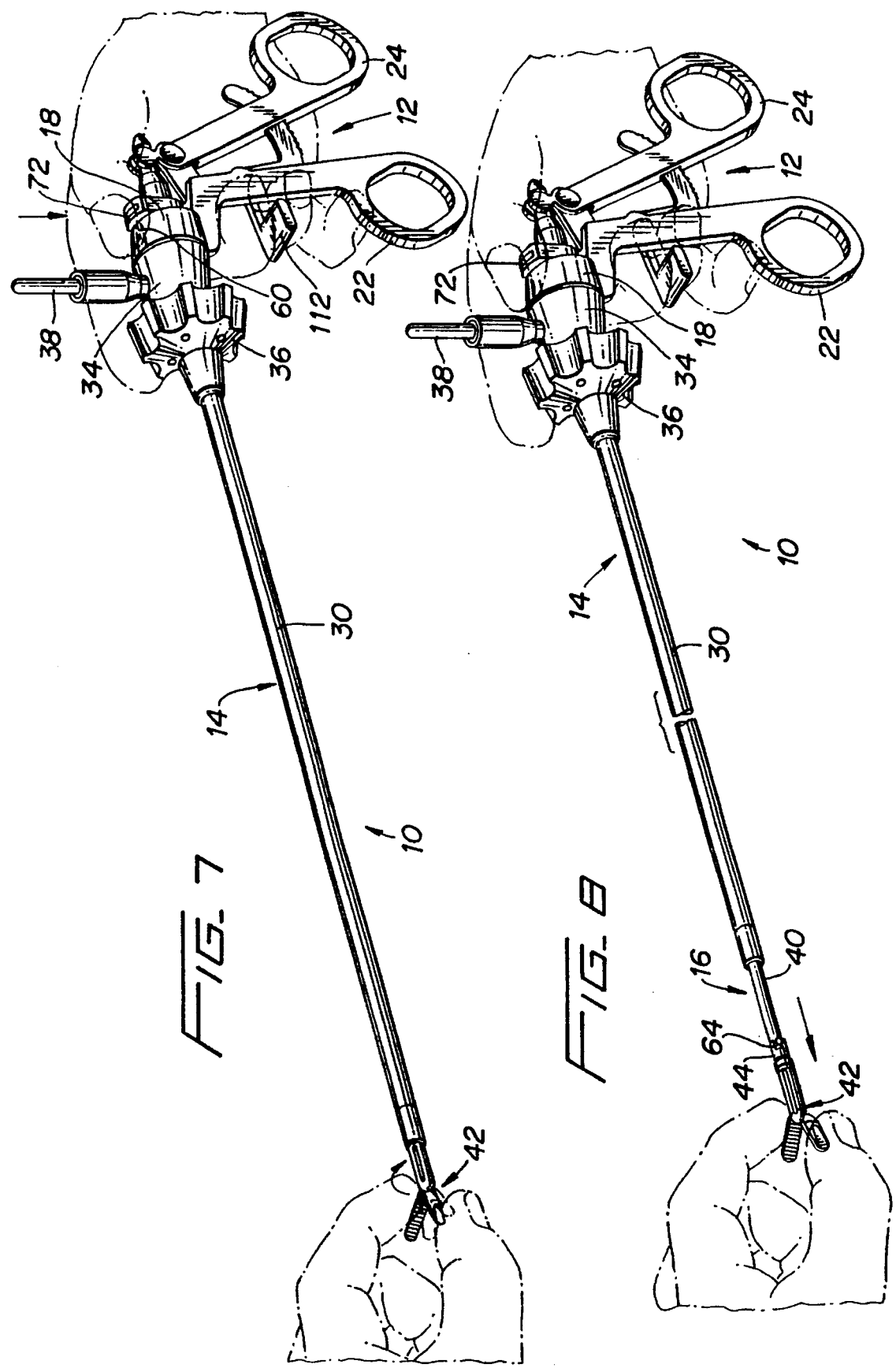

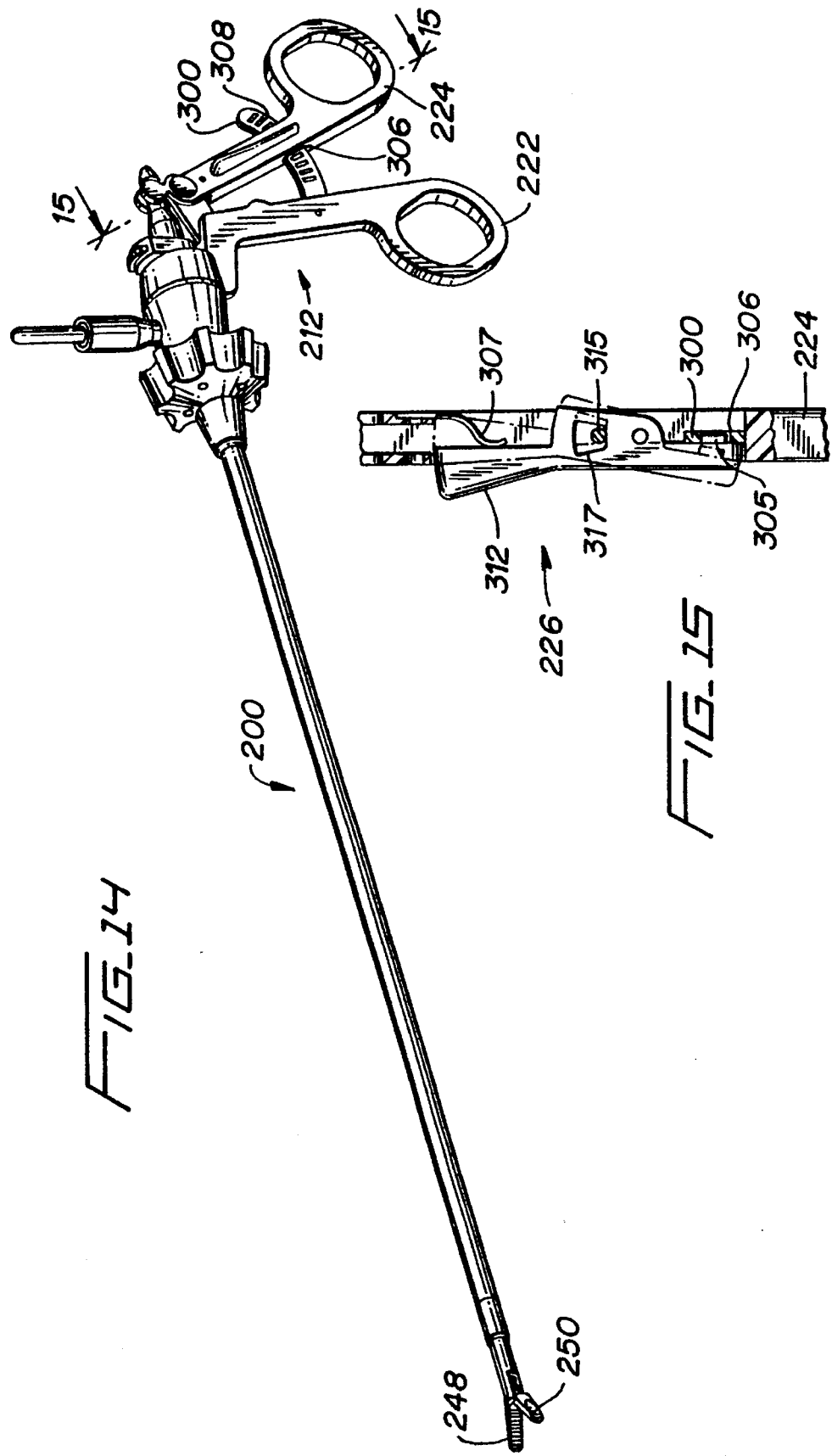

ID=5,603,723

SURGICAL INSTRUMENT CONFIGURED TO BE DISASSEMBLED FOR CLEANING

BACKGROUND

Technical Field

This application relates to surgical instrumentation, and more particularly, to a reusable laparoscopic device that can be disassembled for cleaning. 2. Background of Related Art In laparoscopic surgical procedures, surgery is performed through a small incision formed in a patient's body. The incision provides access for a cannula through which surgical instruments are extended for introduction into the patient's abdominal cavity. A wide variety of surgical instruments are utilized during a laparoscopic procedure including, for example, staplers, clip appliers, graspers, dissectors and retractors.

Traditionally, laparoscopic instruments have been manufactured as reusable devices which can be cleaned and sterilized following a procedure, or disposable devices which are discarded after a single surgical procedure. With disposable devices, cleaning is not required, since they are not reused or resterilized. Reusable instruments must, however, be cleaned and properly sterilized after each surgical procedure. Although techniques such as steam sterilization have been widely used, they are often inadequate to reach all of the blood and tissue residues that can enter a surgical instrument during a surgical procedure. Since laparoscopic instruments are often constructed with an elongated tubular body housing several small mechanical parts, blood and tissue which infiltrates a laparoscopic instrument's body can be particularly difficult to remove. Thus, laparoscopic reusable instruments are often difficult to clean.

Surgeons have recognized the benefits of reusable laparoscopic instruments that can be disassembled for cleaning following a surgical procedure and thereafter reassembled for subsequent utilization. Once disassembled, access to the interior portions of the instrument body and the internal mechanical elements housed therein becomes easier. As a result, traditional cleaning and sterilization methods become more reliable.

An example of a surgical instrument that can be disassembled for improved cleaning is disclosed in U.S. Pat. No. 5,308,358 to Bond et al. The Bond et al. patent describes a device having a threaded coupling for connecting the body of the instrument to the handle assembly, and a similar threaded arrangement for connecting the tool assembly to the distal end of the instrument body. Over time however, threaded connections such as these can become worn or damaged, thereby preventing reassembly of the instrument. Furthermore, the threaded connectors can be accidentally cross-threaded during reassembly, thereby inhibiting proper disassembly of the instrument after utilization. Other surgical instruments configured to be dissembled after utilization are disclosed, for example, in U.S. Pat. Nos. 5,147,357, 5,304,203 and 5,368,606.

It would be beneficial to provide a reusable laparoscopic surgical instrument that can be easily and reliably disassembled for cleaning and subsequently reassembled for utilization.

SUMMARY

A surgical apparatus is provided which is configured to be disassembled for cleaning and reassembled for subsequent utilization. The apparatus includes a handle assembly having a barrel portion, a stationary handle depending from the barrel portion, and an actuating handle pivotally associated with the barrel portion. An elongate body assembly having opposed proximal and distal end portions and an interior bore extending therethrough is releasably engaged within the barrel portion of the handle assembly. An actuation assembly is provided and includes an elongate control shaft dimensioned to extend through the interior bore of the body assembly. A jaw housing is attached to a distal end portion of the control shaft, and a pair of jaw members are supported in the jaw housing and are actuable by the control shaft. The jaw housing is releasably engaged to the body assembly within the interior bore thereof, and a proximal end of the control shaft is releasably engaged to the actuation handle. A release button is mounted in the barrel portion of the handle assembly and includes a spring biased clasp for releasably engaging the control shaft adjacent the proximal end thereof.

In a preferred embodiment of the surgical apparatus of the subject application, the proximal end portion of the elongate body assembly is releasably engaged within the barrel portion of the handle assembly by a bayonette-type connection including an engagement slot formed in the proximal end portion of the body assembly and a corresponding engagement pin provided in the barrel portion of the handle assembly. Similarly, the jaw housing is releasably engaged to the body assembly by a bayonette-type connection including an engagement slot formed in the jaw housing and a corresponding engagement pin provided in the interior bore of the body assembly.

Preferably, a circumferential engagement slot is formed on the control shaft adjacent the proximal end thereof for engagement with the spring biased clasp of the release button, and a wiping member is supported on the control shaft adjacent the proximal end thereof for cleaning the interior bore of the elongate body assembly when the actuation assembly is withdrawn from the body assembly during disassembly of the apparatus. The wiping member preferably includes a plurality of spaced apart circumferential wiping wings which are dimensioned to engage an interior wall surface of the body assembly.

In a preferred embodiment of the surgical apparatus described herein, a rotation control mechanism is provided for rotating the body assembly about a longitudinal axis extending therethrough relative to the handle assembly, and a ratchet mechanism is operatively associated with the stationary handle and the pivoting handle of the handle assembly for selectively maintaining the relative positions thereof.

Further features of the surgical apparatus of the subject application will become more readily apparent from the following detailed description of the apparatus taken in conjunction with the drawings.

BRIEF DESCRIPTION OF THE DRAWINGS

Various embodiments are described hereinbelow with reference to the drawings wherein:

FIG. 4A is an enlarged side elevational view of the wiper disposed on the control shaft of the surgical instrument of FIG. 1 which serves to wipe the internal wall surface of the instrument body as the instrument is disassembled;

FIG. 5 is a side elevational view in cross-section taken along line 5—5 of FIG. 1 illustrating the relative movement of the working components of the surgical instrument of FIG. 1;

FIG. 6 is a cross-sectional view taken along line 6—6 of FIG. 5 illustrating the spring biased clasp which releasably engages the control shaft of the surgical instrument shown in FIG. 1;

FIGS. 7–10 illustrate a series of manipulative steps for disassembling the surgical instrument illustrated in FIG. 1, wherein:

FIG. 7 illustrates movement of the clasp to disengage the control shaft and rotation of the actuation assembly to disengage the jaw housing from the body assembly;

FIG. 8 illustrates withdrawal of the actuation assembly and jaw assembly from the body assembly;

FIG. 9 illustrates rotation of the body assembly to disengage the proximal portion thereof from the handle assembly; and FIG. 10 illustrates detachment of the body assembly from the barrel portion of the handle assembly;

FIG. 14 is a perspective view of another surgical instrument constructed in accordance with a preferred embodiment of the subject application which includes an alternative ratchet mechanism for maintaining the relative position of the handles; and FIG. 15 is a cross-sectional view taken along line 15—15 of FIG. 14 illustrating the operative movements of the ratchet mechanism of the surgical apparatus of FIG. 14.

DETAILED DESCRIPTION OF THE PREFERRED EMBODIMENTS

Figure 1:
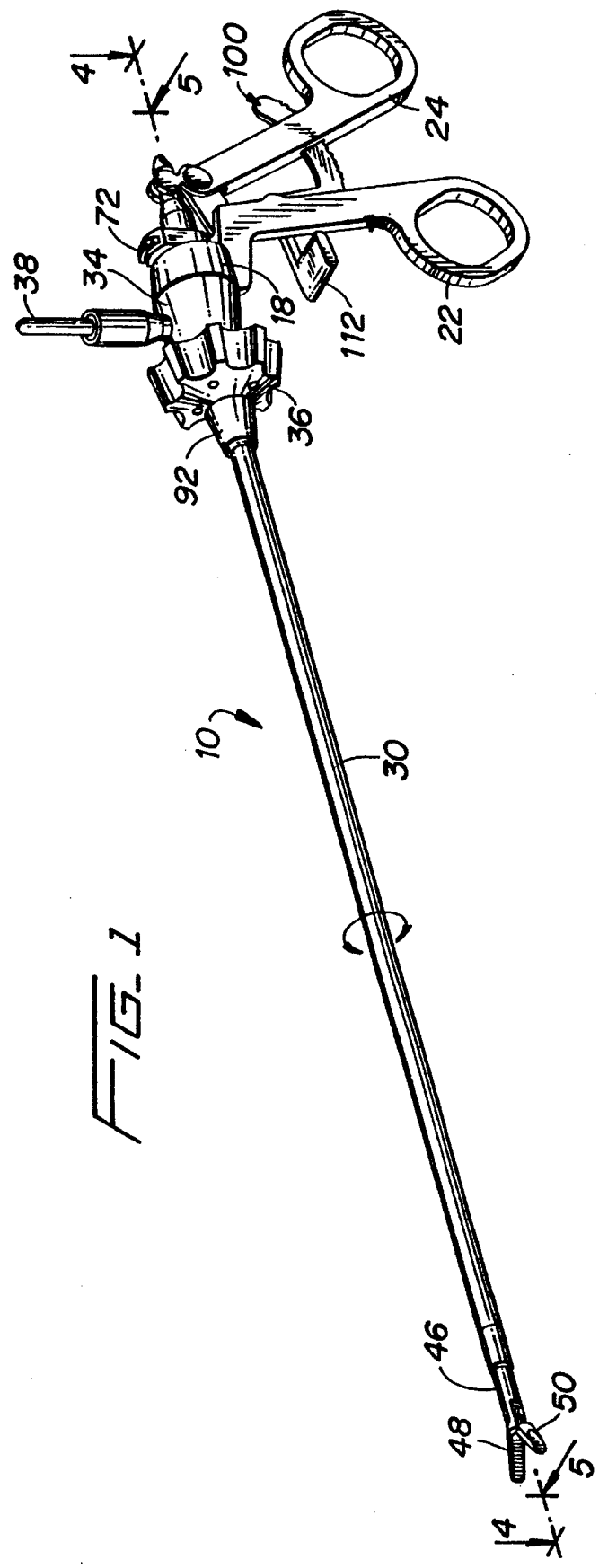
FIG. 1 is a perspective view of a surgical instrument constructed in accordance with a preferred embodiment of the subject application.

In the drawings and in the description which follows, the term "proximal", as is traditional, will refer to the end of the apparatus which is closest to the operator, while the term "distal" will refer to the end which is furthest from the operator.

The surgical apparatus described herein shall be discussed in terms of endoscopic procedures and apparatus. However, use herein of terms such as "endoscopic", "endoscopically", and "endoscopic portion", among others, should not be construed to limit the use to an apparatus for use only in conjunction with an endoscopic tube. To the contrary, it is believed that the surgical apparatus described herein may find use in procedures wherein access is limited to a small incision including but not limited to arthroscopic and/or laparoscopic procedures.

Referring now to the drawings wherein like reference numerals indicate similar structural elements of the subject application, there is illustrated in FIG. 1 a surgical apparatus constructed in accordance with a preferred embodiment of the subject application and designated generally by reference numeral 10. Surgical apparatus 10 is configured as a reusable instrument that can be disassembled for cleaning and subsequently reassembled for utilization.

Figure 2:
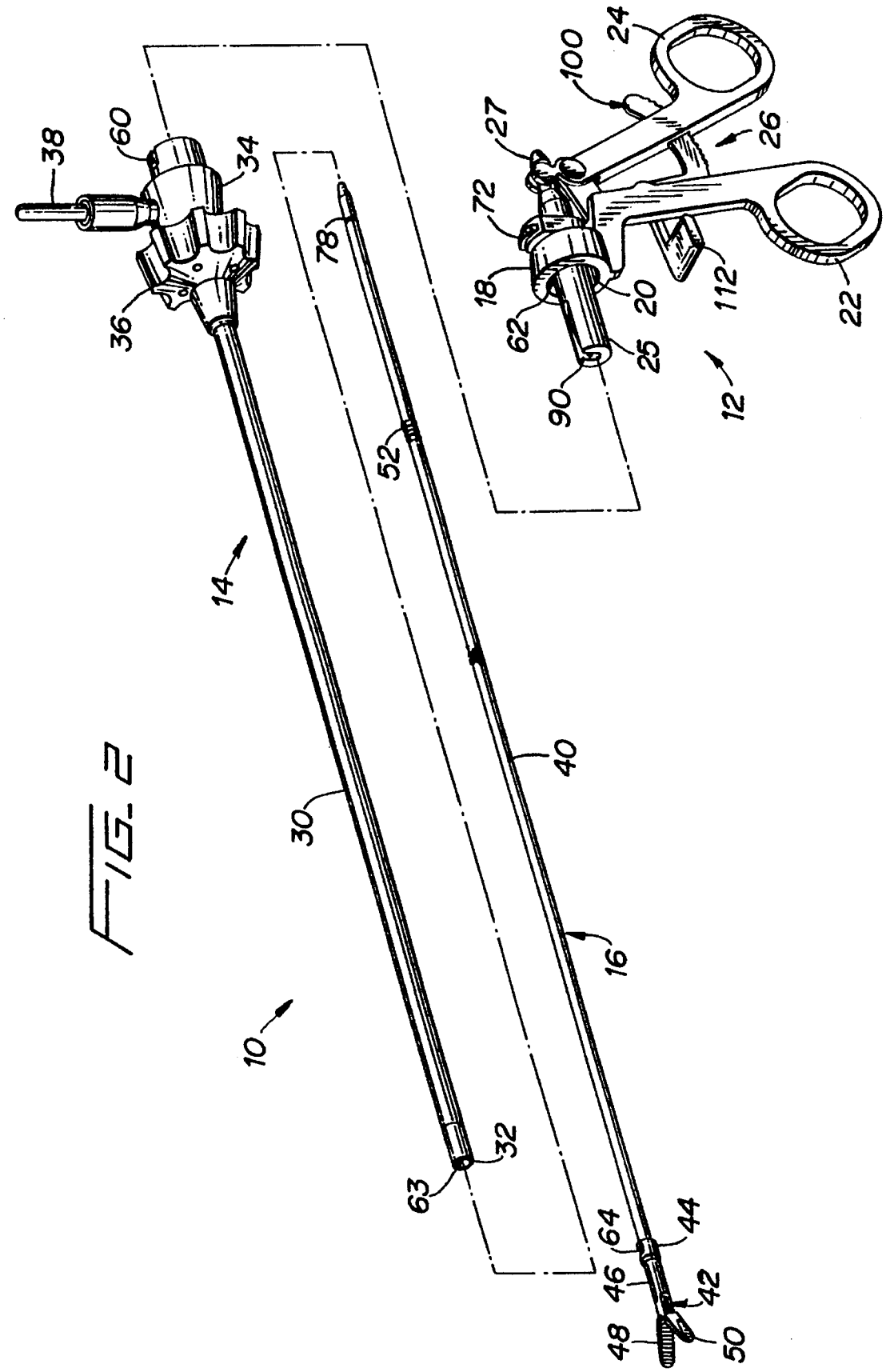
FIG. 2 is a perspective view of the surgical instrument illustrated in FIG. 1 in a disassembled condition wherein the handle assembly, body assembly, and actuation assembly are separated for cleaning.

As best seen in FIG. 2, surgical apparatus 10 has three main structural portions that are easily separated from one another as illustrated in FIGS. 7–10. These portions include a handle assembly 12, an elongated body assembly 14, and an actuation assembly 16.

Figure 3:
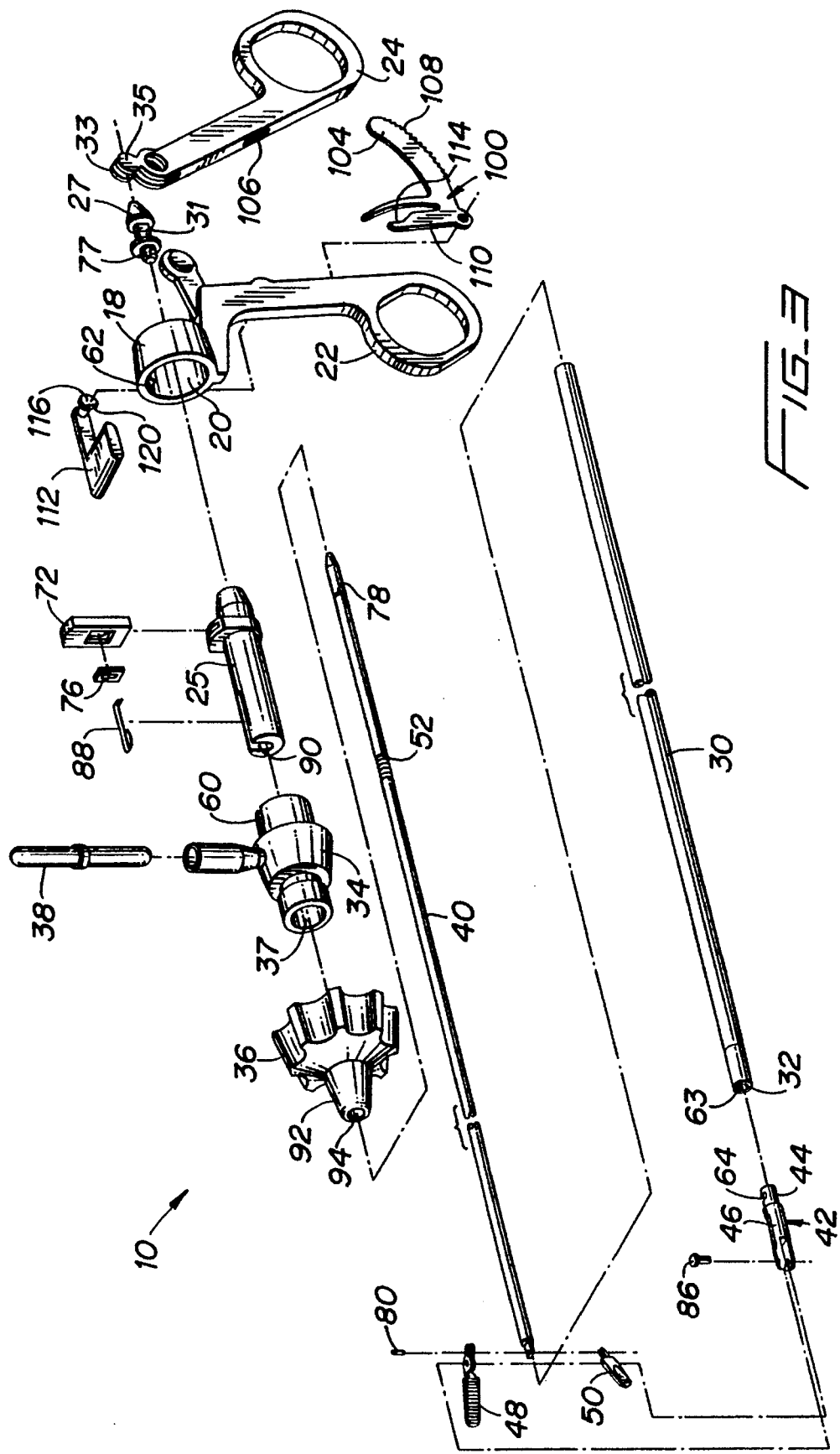
FIG. 3 is an exploded perspective view of the surgical instrument illustrated in FIG. 1 depicting each of the structural and mechanical components thereof.
Figure 4:
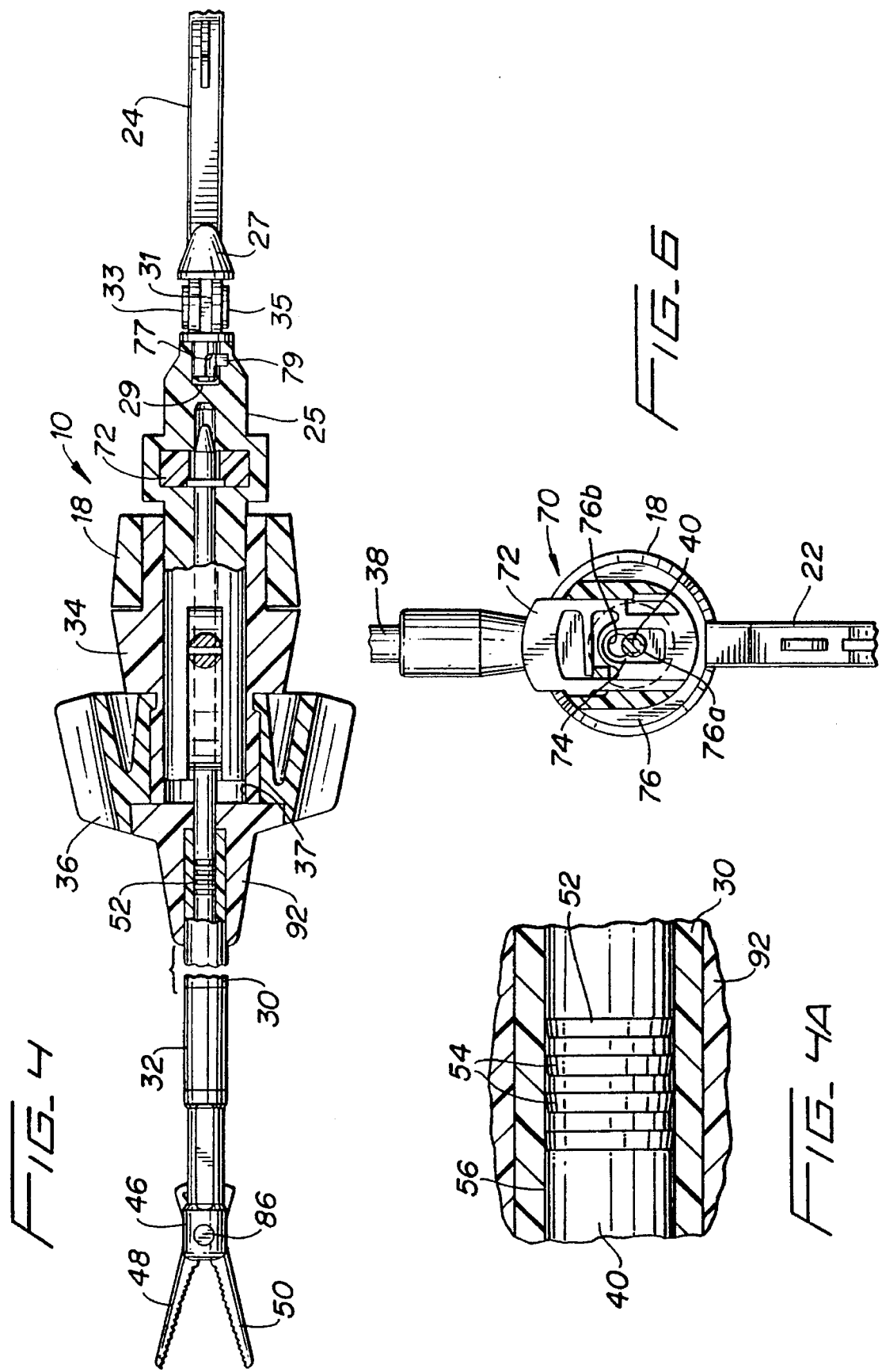
FIG. 4 is a partial cross-sectional view taken along line 4—4 of FIG. 1 illustrating the relationship between the internal components of the surgical instrument.
Figure 11:
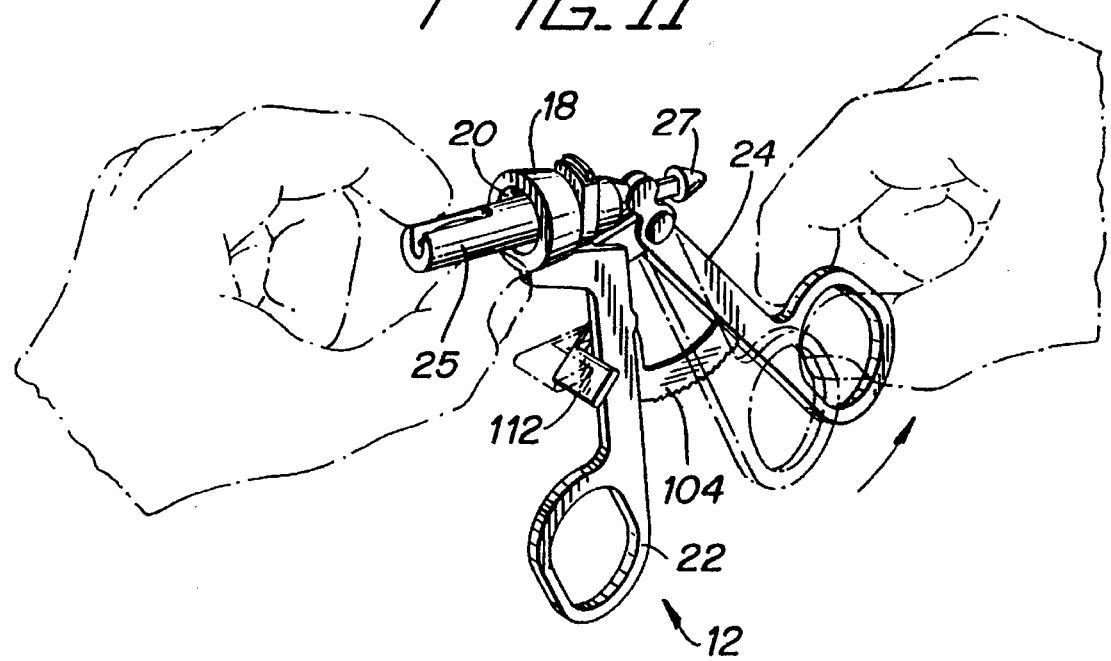
FIGS. 11–13 illustrate a series of manipulative steps for disassembling the handle assembly of the surgical instrument of FIG. 1.

Referring to FIG. 3, handle assembly 12 includes a barrel section 18 defining an axial bore 20, a stationary grip portion depending from barrel section 18, and a pivoting actuation handle 24 adjacent stationary handle 22. Handle assembly 12 is configured for further disassembly into a plurality of subassemblies as illustrated, for example, in FIGS. 11–13. With reference to FIG. 3, these subassemblies include extension shaft 25 and engagement stem 27. Shaft 25 is dimensioned for reception in barrel section 18 and includes an axial bore 29 (FIG. 4). Stem 27 is configured for engagement with actuation handle 24 and includes a generally planar engagement portion 31 for interlocking between a pair of corresponding circular engagement flanges 33 and 35 formed on actuation handle 24. Handle assembly 12 further includes a ratchet mechanism 26 (FIG. 2) which extends between handles 22 and 24 for selectively adjusting the relative positions of the handles, and consequently the relative positions of the cooperating jaws. Ratchet mechanism 26 will be discussed in greater detail hereinbelow with reference to FIG. 5.

With continued reference to FIG. 3, body assembly 14 includes an elongated tubular section 30 defining an axial passageway 32, and a proximal mounting section 34. A rotation knob 36 is associated with mounting section 34 for effecting rotational movement of body assembly 14 and actuation assembly 16 relative to handle assembly 12. A fitting 38 extends from mounting section 34 to connect the instrument to an electrical power source to facilitate utilization of surgical apparatus 10 for electrocauterization. Both of these features are discussed in greater detail hereinbelow.

With continuing reference to FIG. 3, actuation assembly 16 includes an elongate control shaft 40 and a tool assembly 42 associated with a distal end of control shaft 40. Tool assembly 42 includes a base portion 44, a jaw housing 46 depending from base portion 44, and a pair of cooperating jaw members 48 and 50 which are supported in housing 46. Although the jaw members depicted herein are in the form of grasping jaws, it is envisioned that the jaws can take the form of biopsy forceps, cutting blades, needle holding jaws, or dissecting jaws. Other jaw structures can also be employed. The operation and construction of tool assembly 42 is discussed in greater detail hereinbelow.

Referring to FIG. 3 in conjunction with FIG. 4A, a wiping member 52 is provided on control shaft 40 adjacent the proximal end thereof which is dimensioned and configured to clean the axial passageway 32 of tubular section 30 when surgical apparatus 10 is disassembled and actuation assembly 16 is withdrawn from body assembly 14. Wiping member 52 includes a plurality of spaced apart circumferential winglets 54 which engage the internal wall 56 of axial passageway 32 to remove blood and tissue that may have infiltrated the body assembly 14 during a surgical procedure. Wiping member 52 is preferably formed of a resilient polymeric material such as, for example, neoprene. Wiping member 52 also functions as a static seal within the axial passageway 32 of tubular section 30 to inhibit the egress of insufflation gases from the abdominal cavity during a surgical procedure.

Each of the main structural assembles of surgical apparatus 10 and the subassemblies of handle assembly 12 are provided with conventional bayonette-type connective fittings for facilitating convenient and reliable disassembly and reassembly of the apparatus. In general, bayonette-type fittings are configured to detachably connect two structural elements of an apparatus and include a generally J-shaped engagement slot on one of the elements and a corresponding engagement pin on the other element.

Referring now to FIG. 2, a first bayonette-type fitting is provided for detachably connecting handle assembly 12 and body assembly 14. This first connective fitting includes a generally J-shaped engagement slot 60 formed in the mounting section 34 of body assembly 14, and a radially inwardly extending engagement pin 62 disposed in the axial bore 20 of barrel section 18. A second bayonette-type connective fitting is provided for detachably connecting actuation assembly 16 and body assembly 14. This second fitting includes a generally J-shaped engagement slot 64 formed in the base portion 44 of tool assembly 42, and a corresponding radially inwardly extending engagement pin 63 disposed in the axial passageway 32 of tubular section 30 adjacent the distal end thereof. Clearly, alternatively, the engagement pins can be disposed on the mounting section 34 and the base portion 44 of tool assembly 42 to engage slots formed in barrel section 18 and tubular section 30, respectively.

Referring to FIG. 6 in conjunction with FIG. 3, a supplemental locking mechanism 70 is provided for releasably connecting control shaft 40 to extension shaft 25. Locking mechanism 70 is supported in extension shaft 25 and includes a substantially rectangular release button 72 and a spring plate 74 having a notched region 76 for releasably engaging a circumferential slot 78 formed on control shaft 40 adjacent the proximal end thereof. In use, slot 78 is engaged in the lower portion 76a of notched region 76. During disassembly, depression of button 72 causes spring plate 74 to deflect in a generally outward direction, such that the upper portion 76b of notched region 76 associates with control shaft 40. At such a time, spring plate 74 is released from slot 78 and control shaft 40 is disengaged from handle assembly 12.

Thereupon, the disassembly of surgical apparatus 10 into its three main structural components can be effected. As noted above, handle assembly 12 is configured for further disassembly. Thus, a third bayonette-type connection is provided for detachably connecting the subassemblies of handle assembly 12. In particular, referring to FIGS. 12 and 13, a generally J-shaped engagement slot 77 is defined in a distal end of engagement stem 27 and a corresponding radially inwardly extending engagement pin 79 is provided within the axial bore 29 of extension shaft 25.

Figure 5:
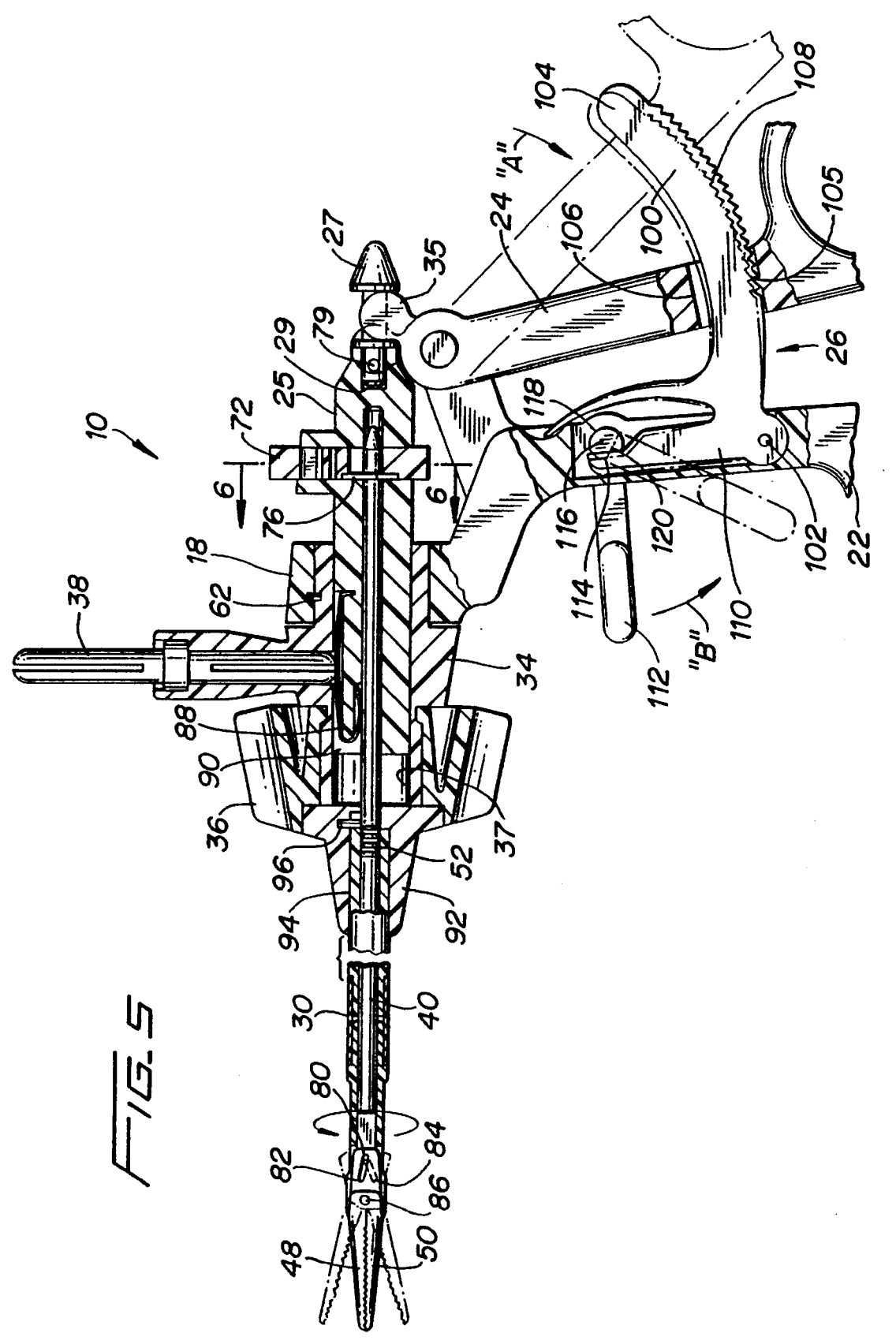

Referring to FIGS. 4 and 5, in operation, the jaw members 48 and 50 of tool assembly 42 are moved between an open position and a closed position through manipulation of actuation handle 24. As best seen in FIG. 5, pivotal movement of actuation handle 24 in the direction indicated by arrow "A" causes circular flanges 33 and 35 to urge engagement stem 27 in a proximal direction. As a result, extension shaft 25 is drawn proximally within the axial bore 37 defined in mounting section 34 of body assembly 14. Consequently, control shaft 40 is pulled in a proximal direction, drawing therewith a cam pin 80 which is associated with the distal end of control shaft 40 and jaw members 48 and 50. More specifically, as best seen in FIG. 5, cam pin 80 is dimensioned and configured to translate relative to a pair of angled cam slots 82 and 84 formed in jaw members 48 and 50 respectively. As cam pin 80 moves relative to cam slots 82 and 84, jaw members 48 and 50 move between open and closed positions as they pivot about a common pivot pin 86 which is supported in jaw housing 46.

With continued reference to FIG. 5, as noted above, a fitting 38 is provided on handle assembly 12 to facilitate utilization of apparatus 10 for electrocauterization during a surgical procedure. In particular, a metallic leaf spring 88 is mounted within a support slot 90 formed in extension shaft 25 which is in contact with control shaft 40 and the cautery fitting 38. Control shaft 40 and jaw members 48 and 50 are preferably formed of an electrically conductive material. Thus, when a current is applied to fitting 38, electrical energy can be delivered to jaw members 48 and 50 through control shaft 40.

Referring to FIG. 5, to effectuate axial rotation of body assembly 14 relative to handle assembly 12, rotation knob 36 is supported on a collar 92 which has an axial cavity 94 for receiving the proximal end of tubular section 30. A set pin 96 retains tubular section 30 within axial cavity 94. Thus, in use, when knob 36 is rotated, collar 92 will also rotate along with the tubular section 30 of body assembly 14. Moreover, since actuation assembly 16 is connected to body assembly 14 through a bayonette-type connection, tool assembly 42 will also rotate with the rotation of knob 36. Rotation of tool assembly 42 is further facilitated by spring plate 74 which permits the rotation of control shaft 40 within notched region 76.

With continued reference to FIG. 5, as discussed briefly hereinabove, surgical apparatus 10 includes a ratchet mechanism 26 for selectively adjusting the relative position of handles 22 and 24. Ratchet mechanism 26 includes a rack member 100 which is pivotably attached to stationary handle 22 by a pivot pin 102. Rack member 100 includes a curved portion 104 which extends through a passageway 106 defined in actuation handle 24. A saw-toothed edge region 108 is formed on curved portion 104 for interacting with a corresponding engagement tooth 105 disposed within passageway 106 of handle 24. Rack member 100 further includes a locking portion 110 which interacts with a pivoting toggle switch 112. Locking portion 110 has a bearing surface 114 for interacting with a bearing post 116 associated with toggle switch 112. Bearing post 116 has a curved surface portion 118 and a flat surface portion 120.

In use, as toggle switch 112 is rotated in the direction indicated by arrow "B ", the curved surface portion 118 of bearing post 116 interacts with bearing surface 114 of locking portion 110, causing rack member 100 to pivot about pin 102. As a result, the saw-toothed edge region 108 of curved portion 104 moves out of engagement with tooth 105. At such a time, ratchet mechanism 26 is disabled and actuation handle 24 can move freely without interference to actuate jaw members 48 and 50. When toggle switch 112 is pivoted into its locking position, in substantial alignment with the longitudinal axis of body assembly 14, (the position shown in FIG. 5) edge region 108 is brought into contact with engagement tooth 105, and the relative positions of handles 22 and 24 can be selectively maintained.

Referring now to FIGS. 7–10, there is illustrated, in sequential order, the manipulative steps for disassembling the main structural portions of surgical apparatus 10, namely, handle assembly 12, body assembly 14, and actuation assembly 16. Initially, as illustrated in FIG. 7, release button 72 is depressed, disengaging the proximal end of control shaft 40 from spring plate 74. Then, tool assembly 42 is rotated to disengage engagement pin 63 of tubular section 30 from engagement slot 64 of tool assembly 42. At such a time, actuation assembly 16 is withdrawn distally from body assembly 14, i.e. tubular section 30, as illustrated in FIG. 8. During this withdrawal stage, wiping member 52 wipes the interior of tubular section 30, removing any blood or tissue residue that may have become deposited therein during a surgical procedure.

Figure 9:
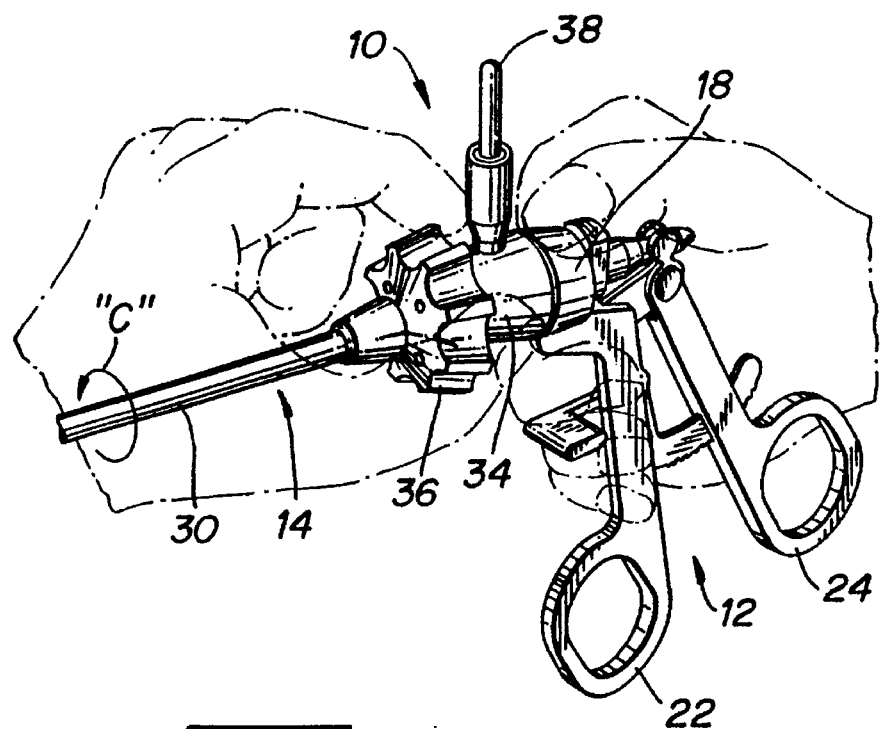
Figure 10:
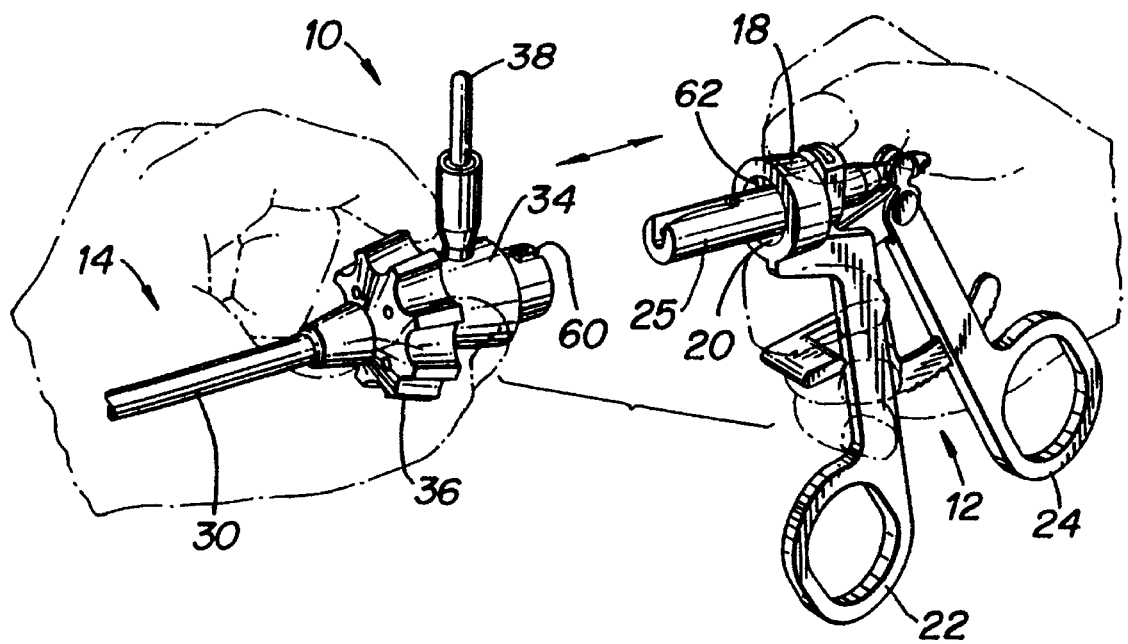

Following the separation of the actuation assembly 16 from the body assembly 14 of surgical apparatus 10, the body assembly 14 is separated from handle assembly 12. Referring to FIG. 9, to separate body assembly 14 from handle assembly 12, mounting section 34 is rotated relative to barrel section 18 in the direction indicated by arrow "C" to disengage engagement pin 62 of barrel section 18 from engagement slot 60 of mounting section 34. At such a time, mounting section 34 is withdrawn from extension shaft 25 as illustrated in FIG. 10.

Figure 12:
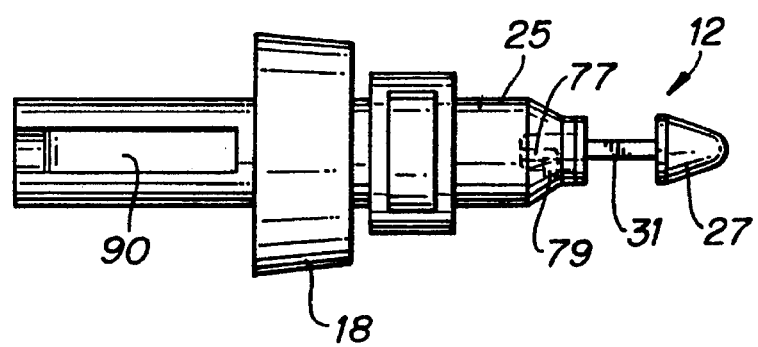
Figure 13:
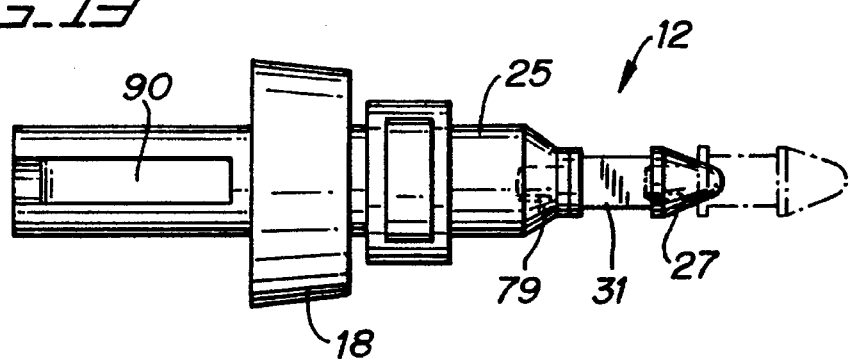

As set forth above, once the handle assembly 12 has been separated from the body assembly 14, it is further separable into a plurality of subassemblies, namely, barrel section 18, extension shaft 25, and engagement stem 27. To disassemble handle assembly 12, ratchet mechanism 26 is first disengaged by releasing toggle switch 112 from its locked position. Actuation handle 24 is then pivoted into a fully rotated position shown in phantom in FIG. 11. Thereafter, as shown in FIGS. 12 and 13, extension shaft 25 is rotated to disengage engagement pin 79 from engagement slot 77. At such a time, extension shaft 25 is withdrawn from barrel section 18 of handle assembly 12. Subsequently, engagement stem 27 may be removed from actuation handle 24. The instrument can now be more easily clean and resterilized, and reassembled for subsequent use.

Turning now to FIGS. 14 and 15, there is illustrated another surgical apparatus constructed in accordance with a preferred embodiment of the subject application and designated generally by reference numeral 200. Surgical apparatus 200 is substantially similar to surgical apparatus 10 in both construction and operation. However, surgical apparatus 200 has a ratchet mechanism 226 associated with handle assembly 212 that differs from the ratchet mechanism 26 of surgical apparatus 10. Ratchet mechanism 226 includes an arcuate rack arm 300 mounted to stationary grip portion 222 and configured to extend through a passageway 306 defined in actuation handle 224. A plurality of spaced apart apertures 308 are defined in rack arm 300 for receiving a locking peg 305 provided on a pivoting toggle switch 312 associated with actuation handle 324. Toggle switch 312 is biased into a locking position by a leaf spring 307.

In operation, to actuate handle 324 and move the cooperating jaw members 248 and 250 between open and closed positions, toggle switch 312 is pivoted in a clockwise direction against the bias of leaf spring 307. The relative movement of toggle switch 312 is limited by a stop peg 315 which cooperates with a port 317 defined in toggle switch 312. To maintain handles 222 and 224 in a desired position with respect to one another, locking peg 305 is selectively engaged in one of the apertures 308 defined in rack arm 300, and toggle switch 312 is released under the bias of leaf spring 307.

It will be understood that various modifications may be made to the embodiments disclosed herein. For example, those skilled in the art will appreciate that various connective fittings can be employed to detachably engage the main structural assemblies of the subject application. Therefore, the above description should not be construed as limiting, but merely as exemplifications of preferred embodiments. Those skilled in the art will envision other modifications within the scope and spirit of the claims appended hereto.

What is claimed is:

1. A surgical apparatus configured to be disassembled for cleaning and reassembled for utilization comprising:
   a) a handle assembly including a barrel portion and an actuation handle pivotally associated with the barrel portion;
   b) an elongate body assembly having opposed proximal and distal end portions and an interior bore extending therethrough, a proximal end portion of the elongate body releasably engaged within the barrel portion of the handle assembly;
   c) an elongate control shaft dimensioned to extend through the interior bore of the body assembly and having opposed proximal and distal end portions, a jaw housing attached to the distal end portion of the control shaft, and a pair of jaw members supported in the housing and actuable by the control shaft, the jaw housing releasably engaged to the body assembly within the interior bore thereof; and
   d) an engaging mechanism associated with the barrel portion of the handle assembly, the engaging mechanism releasably engaging the control shaft adjacent the proximal end thereof, whereby pivotal movement of the actuation handle effectuates cooperative movement of the jaw members between open and closed positions.

2. A surgical apparatus as recited in claim 1, wherein the proximal end portion of the elongate body assembly is releasably engaged within the barrel portion of the handle assembly by a bayonette-type connection.

3. A surgical apparatus as recited in claim 2, wherein the bayonette-type connection includes an engagement slot formed in the proximal end portion of the body assembly and a corresponding engagement pin provided in the barrel portion of the handle assembly.

4. A surgical apparatus as recited in claim 1, wherein the jaw housing is releasably engaged to the body assembly by a bayonette-type connection.

5. A surgical apparatus as recited in claim 4, wherein the bayonette-type connection includes an engagement slot formed in the jaw housing and a corresponding engagement pin provided in the interior bore of the body assembly adjacent a distal end thereof.

6. A surgical apparatus as recited in claim 1, wherein the engaging mechanism comprises a release button mounted in the barrel portion of the handle assembly which includes a spring biased clasp for engaging a circumferential engagement slot formed on the control shaft adjacent the proximal end thereof.

7. A surgical apparatus as recited in claim 1, wherein a wiping member is supported on the control shaft adjacent the proximal end thereof and is configured to clean the interior bore of the elongate body assembly when the control shaft is withdrawn from the body assembly during disassembly of the apparatus.

8. A surgical apparatus as recited in claim 7, wherein the wiping member including a plurality of spaced apart circumferential wiping wings dimensioned to engage an interior wall surface of the body assembly.

9. A surgical apparatus as recited in claim 7, wherein the wiping member is formed of a resilient polymeric material.

10. A surgical apparatus as recited in claim 1, further comprising a rotation control mechanism including a rotation knob operatively associated with the elongate body assembly for rotating the body assembly about a longitudinal axis extending therethrough relative to the handle assembly.

11. A surgical apparatus as recited in claim 1, further comprising a ratchet mechanism operatively associated with the stationary handle and the actuation handle of the handle assembly, the ratchet mechanism selectively maintaining the relative positions thereof.

12. A surgical apparatus as recited in claim 11, wherein the ratchet mechanism includes a toggle switch positioned on the stationary handle and configured to lock the ratchet mechanism in a selected orientation.

13. A surgical apparatus as recited in claim 12, wherein the ratchet mechanism includes a toggle switch positioned on the actuation handle and configured to lock the ratchet mechanism in a selected orientation.

14. A surgical apparatus as recited in claim 1, further comprising an electrocautery fitting operatively associated with the body assembly and a contact member configured to electrically connect the electrocautery fitting and the control shaft.

15. A surgical apparatus as recited in claim 1, wherein said handle assembly is configured for disassembly into a plurality of subassemblies including an extension shaft for connecting the control shaft to the actuation handle.

16. A surgical apparatus configured to be disassembled for cleaning and reassembled for utilization comprising:
 a) a handle assembly including a barrel portion having an interior bore, and an actuation handle pivotally associated with the barrel portion;
 b) an elongate body assembly having opposed proximal and distal end portions and an interior bore extending therethrough, a proximal end portion of the elongate body releasably engaged within the interior bore of the barrel portion of the handle assembly by a first bayonette-type connection;
 c) an elongate control shaft dimensioned to extend through the interior bore of the body assembly and having opposed proximal and distal end portions, a jaw housing attached to the distal end portion of the control shaft, and a pair of jaw members supported in the housing and actuable by the control shaft, the jaw housing releasably engaged to the body assembly within the interior bore thereof by a second bayonette-type connection; and
 d) a spring biased release button mounted in the barrel portion of the handle assembly, the release button releasably engaging the control shaft adjacent the proximal end thereof, said control shaft being further connected to the actuation handle such that movement of the actuation handle effectuates cooperative movement of the jaw members between open and closed positions.

17. A surgical apparatus as recited in claim 16, wherein the first bayonette-type connection includes an engagement slot formed in the proximal end portion of the body assembly and a corresponding engagement pin provided in the barrel portion of the handle assembly.

18. A surgical apparatus as recited in claim 17, wherein the second bayonette-type connection includes an engagement slot formed in the jaw housing and a corresponding engagement pin provided in the interior bore of the body assembly adjacent a distal end thereof.

19. A surgical apparatus as recited in claim 16, wherein the release button includes a spring biased clasp configured to engage a circumferential engagement slot formed on the control shaft adjacent the proximal end thereof.

20. A surgical apparatus as recited in claim 1, wherein a wiping member including a plurality of spaced apart circumferential wiping wings is supported on the control shaft adjacent the proximal end thereof to clean the interior bore of the elongate body assembly when the actuation assembly is withdrawn from the body assembly during disassembly of the apparatus.

21. A surgical apparatus as recited in claim 1, further comprising a rotation control knob operatively associated with the elongate body assembly, wherein movement of the rotation control knob effects rotation of the body assembly about a longitudinal axis extending therethrough relative to the handle assembly.

22. A surgical apparatus configured to be disassembled following a surgical procedure comprising:
 a) a handle assembly including a barrel portion defining an interior bore;
 b) an elongated body assembly releasably engaged within the interior bore of the barrel portion, the elongated body defining an interior bore;
 c) a control shaft releasably engaged within the interior bore of the body assembly and operatively connected to the handle assembly;
 d) a tool assembly operatively associated with a distal end portion of the body assembly and actuable by the control shaft; and
 e) a wiping member operatively associated with at least one of the body assembly and the control shaft for cleaning the interior bore of at least one of the barrel portion and the body assembly when the apparatus is disassembled following a surgical procedure.

* * * * *